United States Patent
Joulain et al.

(10) Patent No.: US 7,816,566 B2
(45) Date of Patent: Oct. 19, 2010

(54) *P*-MENTHAN-3-OL ALKYLATED DERIVATIVES AND THEIR USE AS REFRESHING AGENTS

(75) Inventors: Daniel Joulain, Grasse (FR); Claudio Fuganti, Milan (IT); Stefano Serra, Usmate-Velate (IT); Andrea Vecchione, Bologna (IT)

(73) Assignee: Robertet S.A., Grasse (FR)

( * ) Notice: Subject to any disclaimer, the term of this patent is extended or adjusted under 35 U.S.C. 154(b) by 310 days.

(21) Appl. No.: 11/579,654

(22) PCT Filed: Apr. 28, 2005

(86) PCT No.: PCT/FR2005/001058

§ 371 (c)(1),
(2), (4) Date: Nov. 17, 2008

(87) PCT Pub. No.: WO2005/121058

PCT Pub. Date: Dec. 22, 2005

(65) Prior Publication Data

US 2009/0163733 A1 Jun. 25, 2009

(30) Foreign Application Priority Data

May 13, 2004 (FR) .................................. 04 05210

(51) Int. Cl.
*C07C 35/08* (2006.01)
*C07C 35/12* (2006.01)
*A61K 8/18* (2006.01)

(52) U.S. Cl. .................... 568/822; 568/829; 512/25
(58) Field of Classification Search ................ 568/822, 568/829; 512/25

See application file for complete search history.

(56) References Cited

FOREIGN PATENT DOCUMENTS

FR 2 359 604 2/1978
GB 1315626 * 5/1973

OTHER PUBLICATIONS

M. Perry et al., Bull. Soc. Chim FR., No. 10, 1969, pp. 3574-3580, XP008037722.
J. Kulesza et al., Riechstoffe, Aromen, Korperpflegemitttel, vol. 24, No. 8, 1974, pp. 226-229 XP001167005.
S. Panev et al., Tetrahedron Asymmetry, vol. 12, No. 9, 2001, pp. 1313-1321 XP004250309.

* cited by examiner

*Primary Examiner*—Sikarl A Witherspoon
(74) *Attorney, Agent, or Firm*—Browdy and Neimark, PLLC

(57) ABSTRACT

The invention concerns a 3-alkylated crystallized (1R,4S)-p-menthan-(3)-ol derivative, of formula A or B, wherein: either when R<2> represents hydrogen or a methyl radical, R<1> represents a —(CH2)n-OH where n can be 1, 2 and 3, or when R<2> represents a hydroxy radical, R<1> represents a methyl radical or a —(CH2)n-OH group where n can be 1, 2 and 3. The invention also concerns methods for preparing same, and perfume, cosmetic or food compositions containing said derivative.

19 Claims, No Drawings

P-MENTHAN-3-OL ALKYLATED DERIVATIVES AND THEIR USE AS REFRESHING AGENTS

The present invention relates to novel crystallized p-menthan-3-ol alkylated derivatives and their application, in particular as refreshing agents.

There is a continued need for substances producing an effect of freshness in the mouth or on the skin. In the case of food, including drinks, sweets, chewing gums and dental, body or medicated hygiene products, substances which specifically produce a sensation of cold, without contributing any other effect as regards aroma or taste are especially sought. Numerous chemically defined substances are already known which are endowed with an intense refreshing power. The best known is l-menthol, the main component of certain essential oils of mint (Mentha spp.), for example Mentha arvensis, from which it can be isolated in a state of very high purity by crystallization. Whether it is of natural or synthetic origin, thanks to its moderate price, menthol has numerous uses in food and dental hygiene preparations. However, in addition to its too high volatility, l-menthol has several other drawbacks, including a typical odour which is clearly reminiscent of mint, as well as a bitter taste, which make it unsuitable in formulations for which these attributes are undesirable. Furthermore, it can cause a burning sensation when it is used at a high concentration, and can sometimes produce interactions with other components of aromatic mixtures.

For this reason, for a long time, the synthesis of the substances has been researched which produce the most intense and lasting possible physiological sensation of freshness, with an absence of bitterness and odour.

It would also be desirable to have such substances in crystallized form.

A first solution involves increasing the molecular weight of the menthol while preserving its basic structure. Hydroxylated menthol derivatives such as hydroxy-8-p-menthan-3-ol are described in U.S. Pat. No. 5,959,161. Menthyl monosuccinate and its uses as a refreshing agent are claimed in U.S. Pat. Nos. 5,725,865 and 5,843,466. Similarly, the corresponding monoglutarate is described in WO 2003/043431. Mixed menthyl and polyol carbonates such as glycerol and propylene-glycol, described in U.S. Pat. No. 3,419,543 are also good candidates. l-menthyl lactate is described in DE-A-2 608 226.

Another solution involves grafting a radical substituted by alkyl and hydroxyl groups onto the menthol in order to obtain derivatives carrying the menthoxy radical. Thus, it has been noted that numerous derivatives of this category correspond to the requirements explained previously. There can be mentioned inter alia (−)-menthoxypropane-1,2-diol described in U.S. Pat. No. 4,459,425 by Takasago Perfumery Co. Cyclic acetals of menthone are related to this category, such as the glycerol acetal described in U.S. Pat. No. 5,266,592.

Another category of refreshing products with a p-menthan-3-yl skeleton is that in which a carboxamide function is grafted onto the ring. Among the numerous derivatives which have been synthesized and claimed in various patents by Wilkinson Sword Ltd., N-ethyl-p-menthane-3-carboxamide, known as WS-3, is still produced and widely used at present. It has also been found that the p-menthan-3-yl unit is not indispensable and that suitably substituted N-alkylcarboxamides can be very active; this is the case with 2-isopropyl-N,2,3-trimethylbutyramide, also known as WS-23.

Recently, the Nestec company discovered in roasted malt certain pyrrolidinyl furanone derivatives, and in particular 4-methyl-3-(1-pyrrolidinyl)-2[5H]furanone, endowed with a very intense refreshing effect. The use of these substances as refreshing agents is claimed in U.S. Pat. No. 6,592,884. However, under the usual conditions of use of products with a refreshing effect, the use of these enamines is impeded by their relatively poor stability, with the production of an unpleasant odour of pyrrolidine and significant browning.

The French application No. 2 359 604 describes the use of a menthol derivative having a 2-hydroxyethyl group on the carbon 3 of the p-menthanyl unit, as a novel refreshing substance. In fact, the 3-hydroxy-p-menthan-3-ethanol obtained according to the method described in this document has the appearance of a syrupy liquid, constituted by at least two pairs of stereoisomers, each in a proportion of approximately 85:15. It was subsequently observed that the process for obtaining this mixture was also the cause of the presence of several other minor components which negatively alter the expected performance, mainly by the presence of a perceptible mentholated odour, and a bitter taste.

Surprisingly, the Applicant has discovered that novel 3-alkylated crystallized (1R,4S)-p-menthan-3-ol derivatives produced an intense and lasting physiological sensation of freshness, with an absence of bitterness and odour.

This is why a subject of the present application is a 3-alkylated crystallized (1R,4S)-p-menthan-3-ol derivative, of formula A or B;

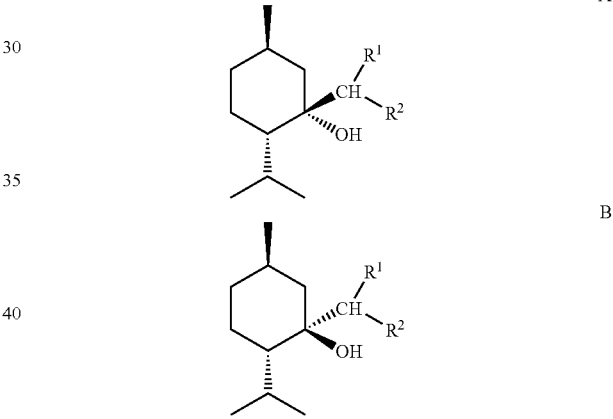

in which, either when $R^2$ represents hydrogen or a methyl radical, $R^1$ represents a —$(CH_2)$n-OH group where n can take the values 0, 1, 2, and 3, or when $R^2$ represents a hydroxy radical, $R^1$ represents a methyl radical or a —$(CH_2)$n-OH group where n can take the values 1, 2, and 3.

Under preferential conditions for implementation of the invention, $R^2$ represents hydrogen or a methyl radical. Under other preferential conditions for implementation of the invention, $R^2$ represents a hydroxy radical. Under yet other preferential conditions for implementation of the invention, n has the value 0, 1 or 2 and particularly the value 0 or 1.

Among the compounds of the invention there can more particularly be mentioned
(−)-(1R,3R,4S)-3-hydroxy-p-menthane-3-ethanol 1a,
(−)-(1R,3R,4S)-3-hydroxy-p-menthane-3-ethanol 1b,
(−)-(1R,3R,4S)-3-hydroxy-p-menthane-3-methanol 2a,
(−)-(1R,3R,4S)-3-hydroxy-p-menthane-3-methanol 2b The formulae of the compounds identified are included at the end of the description.

A subject of the present application is also a process for the preparation of a 3-alkylated crystallized (1R,4S)-p-menthan- 3-ol derivative of formula A or B above in which R2 represents H and R1 represents a —(CH$_2$)n-OH group where n is equal to 1, characterized in that a Reformatzky reaction is carried out between an alkyl α-halogenoacetate and more than 95% pure (−)-menthone, followed by the reduction of the β-hydroxyester thus obtained to 1,3-diol using a hydride such as LiAlH$_4$ in order to obtain the expected 3-hydroxy-p-menthan-3-ethanol isomers.

A subject of the present application is also a process for the preparation of a 3-alkylated crystallized (1R,4S)-p-menthan-3-ol derivative of formula A above in which R$^2$ represents hydrogen and R$^1$ represents a —(CH$_2$)n-OH group where n=0, characterized in that a vinylmagnesium halide such as vinylmagnesium bromide is condensed with the (−)-menthone, followed by acetylation of the tertiary vinylcarbinol obtained, then by an ozonolysis process in order to obtain an ozonide which is preferably reduced in situ, in particular using sodium borohydride, then hydrolysis of the acetate thus formed, in order to obtain the expected 1,2-diol, which is isolated and if desired purified for example by crystallization.

A subject of the present application is also a process for the preparation of a 3-alkylated crystallized (1R,4S)-p-menthan-3-ol derivative of formula B above in which R$^2$ represents hydrogen and R$^1$ represents a —(CH$_2$)n-OH group where n=0 characterized in that (−)-menthone cyanhydrin is selectively prepared, then reduced with a hydride in order to obtain the expected 1,2-diol, which is isolated and if desired purified for example by crystallization.

A subject of the present application is also a process for the preparation of a 3-alkylated crystallized (1R,4S)-p-menthan-3-ol derivative of formula A above in which R$^2$ represents a hydroxy radical and R$^1$ represents a —(CH$_2$)n-OH group where n=0 characterized in that a vinylmagnesium halide, such as vinylmagnesium bromide is condensed with (−)-menthone, followed by epoxidation of the tertiary vinylcarbinol obtained, then alkaline hydrolysis is carried out, in order to obtain the expected triol, which is isolated and if desired purified for example by crystallization.

The p-menthane-3-ol derivatives which are the subject of the present invention have very useful properties and qualities. They produce in particular a sensation of freshness, without production of the characteristic odour of menthol and without bitterness.

These properties justify the use of the p-menthane-3-ol derivatives described above, in perfumery and cosmetology.

This is why a subject of the present application is also a perfume or cosmetic composition, or also a food composition, characterized in that it contains a p-menthane-3-ol derivative described above, in particular as a refreshing agent or for its mentholated odour.

These compositions can be, for example, solids or liquids and be presented in the forms commonly used, for example non-limitatively: lotions, after-shave lotions, toilet waters, deodorants, shampoos, shaving creams, toothpastes and other dental hygiene products, ointments, aerosols, the flavouring of food products including: sweets, chewing-gums, icecreams, drinks, mentioned non-limitatively, and tobaccos; they are prepared according to the usual methods.

The p-menthane-3-ol derivative or derivatives can be incorporated into the excipients usually used in these compositions, such as gum arabic, lactose, starch, aqueous or non-aqueous vehicles and preservatives.

A subject of the present invention is also a process for the preparation of a composition described above, characterized in that, according to methods known per se, the p-menthane-3-ol derivative or derivatives are mixed with acceptable ingredients.

The preferential conditions for use of the p-menthane-3-ol derivatives described above also apply to the other subjects of the invention referred to above, in particular perfume or cosmetic compositions.

The examples which follow illustrate the present application.

EXAMPLES 1 AND 2

(−)-(1-R,3R,4S)-3-hydroxy-D-menthane-3-ethanol 1a and (−)-(1R,3S,4S)-3-hydroxy-p-menthane-3-ethanol 1b A solution of 0.1 mole of 85% pure (−)-menthone and 0.16 mole of ethyl bromoacetate in 100 ml of tetrahydrofuran (THF) is added slowly to a boiling and stirred suspension of 0.3 mol of zinc in the powder form which has been previously activated with a small quantity of iodine. As soon as the reaction has been initiated, the heating is interrupted and the addition is carried out so that the exothermic reaction maintains reflux of the solvent. Once the addition is completed, heating is resumed for an hour. The cooled down reaction mixture is filtered on Celite, then the latter is washed with 250 ml of THF then 250 ml of ethyl acetate.

The combined organic phases are washed successively with a dilute solution of hydrochloric acid and with salt water. The organic phase is dried and the solvents are evaporated off. The residue is subjected to chromatography on silica gel, using hexane containing increasing proportions of ethyl acetate as elution solvent. The two Reformatzky diastereoisomeric adducts are thus isolated in the proportion 4:1 (yield 70-75%).

Each separated hydroxy-ester, in 20% solution in dry THF, is added to a boiling suspension of 1.5 molar equivalents of lithium aluminium hydride in THF.

After three hours of reflux, the reaction medium is cooled down and ethyl acetate and dilute hydrochloric acid are successively added. The organic phase is separated, and the aqueous phase is extracted with ethyl ether. The combined organic phases are dried and the solvents removed.

The residue is chromatographed on a small silica gel column, using a hexane-ethyl acetate mixture 95:5 as elution solvent. An oil is obtained which solidifies. The crude solid is then crystallized from 1.5 to 2 volumes of hexane, in order to produce each of the two diastereoisomeric diols with a yield of 70-80%.

Analyses:

(−)-(1R,3R,4S)-3-hydroxy-p-menthane-3-ethanol 1a. MP 80-82° C.; [α]D −16°; NMR 1H δ 0.77-0.98 (2H, m), 0.90 (3H, d, J=6.5 Hz), 0.91 (6H, d, J=6.7 Hz), 1.03 (1H, ddd, J=12.9, 3.5, 2.0 Hz), 1.27-1.59 (3H, m), 1.60-1.93 (3H, m), 2.12-2.36 (2H, m), 2.23 (2H, 3.70-3.83 (1H, m), 3.99 (1H, ddd, J=14.5, 10.3, 4.1 Hz); NMR 13C δ 17.6, 20.0, 22.1, 23.3, 25.2, 27.5, 34.6, 40.5, 45.9, 49.7, 58.6, 75.0; mass spectrum: m/z 200 (M+), 185, 155, 137, 115 (100%), 97, 81, 69, 55; IR spectrum (nujol): ν (cm−1) 856, 1072, 3299, 3378.

(−)-(1R,3S,4S)-3-hydroxy-p-menthane-3-ethanol 1b. MP 84-86° C.; [α]D −33.4°; NMR $^1$H δ 0.80-1.02 (1H, m), 0.85 (3H, d, J=6.7 Hz), 0.90 (3H, d, J=6.2 Hz), 0.98 (3H, d, J=6.7 Hz), 1.1 (2H, m), 1.26-1.50 (1H, m), 1.57-1.80 (3H, m), 1.83-2.00 (1H, m), 2.04-2.26 (2H, m), 2.30 (2H, s), 3.72-3.85 (1H, m), 3.93 (1H, ddd, J=13.9, 10.8, 3.1 Hz); NMR $^{13}$C δ 19.6, 22.4, 24.1, 24.8, 24.9, 30.3, 32.6, 35.1, 47.1, 54.1, 59.2, 77.1; mass spectrum: m/z 200 (M+), 185, 155, 149, 143, 137, 129, 121, 115 (100%), 97, 88, 81, 69, 55; IR spectrum: (nujol): ν (cm−1) 866, 871, 1157, 3308.

These two diols have an intense refreshing effect, above all without appreciable bitterness or mentholated odour.

EXAMPLE 3

(−)-(1R,3R,4S)3-hydroxy-p-menthane-3-methanol 2a

Firstly a solution of vinylmagnesium bromide is prepared using 0.15 mole of magnesium turnings and 0.13 mole of 15% vinyl bromide in solution in THF. This solution is added under nitrogen to a solution of 0.1 mole of (−)-menthone in 80 ml of THF, at a temperature comprised between −20° and −30° C. After stirring for two hours, the reaction mixture is brought to ambient temperature, followed by cooling down to 0° C., and addition of an ammonium chloride solution. The aqueous phase is decanted and extracted twice with 100 ml of ethyl acetate. The combined organic phases are successively added to an iced solution of 0.1 N hydrochloric acid, saturated sodium bicarbonate then to salt water. After drying over sodium sulphate, the oily residue (16.3 g) obtained after elimination of the solvents, is dissolved in 100 ml of acetic anhydride, to which 2.5 g (0.03 mole) of sodium acetate is added. This mixture is brought to the boil under stirring for 5 hours. After cooling down, the reaction mixture is poured onto crushed ice. After being left for 2 hours at ambient temperature, the mixture is extracted twice with 250 ml of a mixture of hexane and ethyl acetate 1:1. The organic phase is then washed several times with water, then with a saturated solution of sodium bicarbonate and finally with salt water. The oily residue obtained after drying and evaporation of the solvents is chromatographed on 200 g of silica gel (MN Kieselgel 60—Macherey & Nagel), carrying out elution with a hexane/ethyl acetate mixture 4:1. Thus 11.2 g (yield 50%) of acetylated vinyl carbinol, and 20% of unchanged vinyl carbinol are collected. The acetylated derivative is dissolved in 80 ml of a mixture of methanol and dichloromethane, then subjected to ozonolysis at −70° C. Any excess ozone is eliminated by bubbling nitrogen through the reaction mixture followed by treating it with a solution of sodium borohydride in ethanol (1 molar equivalent). The temperature is raised to 20-25° C., then, after two hours, the reaction mixture is diluted in iced water, then extracted twice with 150 ml of dichloromethane. After evaporation of the solvents, the residue is dissolved in 100 ml of methanol then heated in a water bath for 2 hours avec 10 ml of a 40% potash solution in water. The methanol is evaporated off at low temperature under reduced pressure, then diluted in iced water and the pH adjusted to 5 using acetic acid. The reaction mixture is then extracted twice with 100 ml of dichloromethane. After elimination of the solvent, a crude product remains which is crystallized from 2 volumes of hexane with cooling down overnight at −20° C.; 6.3 g of the desired product 2a (yield 73%) is obtained.

Analyses:

MP. 80-2° C.; [α]D −6.7°; NMR $^1$H δ 0.77-1.05 (2H, m), 0.90 (3H, d, J=6.2 Hz), 0.91 (6H, d, J=7.0 Hz), 0.18 (1H, ddd, J=6.6, 4.3, 2.3 Hz), 1.35-1.60 (2H, m), 1.61-1.84 (3H, m), 1.66 (2H, s), 2.08 (1H, dh, J=2.3; 7.0 Hz), 3.43 (1H, d, J=10.8 Hz), 3.73 (1H, d, J=10.8 Hz); NMR $^{13}$C δ 18.2, 20.5, 22.4, 23.6, 26.1, 27.8, 35.1, 44.9, 47.4, 63.4, 75.0; mass spectrum: m/z 186 (M+), 155 (100%), 137, 125, 111, 101, 95, 81, 74, 69, 55, 43; IR spectrum (nujol): v (cm−1) 819, 906, 1042, 1165, 1265, 3219, 3526.

EXAMPLE 4

(−)-(1R,3S,4S)-3-hydroxy-p-menthane-3-methanol 2b

Boron trifluoride etherate (7.8 ml, 58 mmol) and trimethylsilyl cyanide (7.2 ml, 58 mmol) are added to 10 g of (−)-menthone (13 ml, 64 mmol). The mixture is stirred for one hour at ambient temperature, then at 60° C. for 30 minutes. The reaction is interrupted by adding whilst cold 100 ml of an aqueous solution of 2N hydrochloric acid. The mixture is extracted with ether (3 times 100 ml), the combined organic extracts are washed with a 5% sodium bicarbonate solution, then with salt water. After drying over sodium sulphate, and evaporation of the solvents, the residue is chromatographed on a silica gel column, with elution with a hexene/ether mixture 9:1. Thus 4 g of the desired cyanhydrin (with the cyano group in axial configuration) is isolated i.e. a yield of 38%.

This cyanhydrin (3 g, 17 mmol) is dissolved in 75 ml of anhydrous toluene under nitrogen. While cooling down to −40° C., di-isobutylaluminium hydride (30 ml of a 1.2M solution in toluene) is added over one hour. After the addition is completed, stirring is maintained at this temperature for one hour. Then the reaction mixture is poured into a stirred mixture of 40 ml of a saturated solution of iced ammonium chloride (40 ml) and ether (40 ml). Then 60 ml of an aqueous 5% sulphuric acid solution is added and the mixture is stirred vigorously for two hours at ambient temperature. The reaction mixture is then extracted with ether (twice 100 ml), and the combined organic phases are concentrated under reduced pressure. The residue is dissolved in 50 ml of methanol and treated at ambient temperature with sodium borohydride (20 mmol, 0.76 g). The usual treatments provide 2.1 g of a crude product which is then purified by chromatography on a silica gel column, with elution by a hexane/ethyl acetate mixture 4:1 then 1:1. Then 1.9 g of pure diol 2b is obtained.

Analyses:

MP 48-50° C.; [α]D−19.6°; NMR 1H δ 0.73-1.02 (2H, m), 0.79 (3H, d, J=7.0 Hz), 0.91 (3H, d, J=7.0 Hz), 0.97 (3H, d, J=7.0 Hz), 1.1 (1h, dq, J=13.1, 3.1 Hz), 1.23-1.36 (1H, m), 1.38-1.58 (1H, m), 1.64 (1H, ddd, J=10.1, 6:6, 3.1 Hz), 1.70-1.81 (1H, m), 2.04-2.24 (2H, m), 3.15 (2H, bs), 3.63 (1H, d, J=11.2 Hz), 3.69 (1H, d, J=11.2 Hz); NMR 13C δ 19.5, 22.4, 23.6, 24.7, 30.1, 35.0, 44.9, 52.0, 62.9, 76.4; EI-MS m/z 186 (M+), 169, 155, 137, 111, 101, 95, 83, 81, 69, 59, 55, 43, 41.

EXAMPLE 5

(1R,3R,4S)-3-hydroxy-p-menthane-3-(ethane-1,2-diol) 3

3-chloroperbenzoic acid (1.1 molar equivalent of a 70% suspension in water) is added by portions to a solution of the preceding vinyl carbinol (0.1 mole) in 100 ml of dichloromethane, while stirring at 0° C. After 10 hours, the 3-chlorobenzoic acid precipitate is filtered through a Buchner. The filtrate is washed with a saturated solution of sodium bicarbonate. After purification by chromatography on a silica gel column, the epoxycarbinol is obtained in the form of an oil, with a yield of 80%, then dissolved in 70 ml of THF, followed by the addition of 0.5 molar equivalent of lithium hydroxide dissolved in a minimum amount of water, and the mixture is stirred at 50° C. for 2 hours. The volume of the reaction mixture is reduced by evaporation of the solvent under reduced pressure and separated into a mixture of water and ether. The organic phase is washed with a dilute solution of hydrochloric acid then with salt water. After elimination of the solvents, the expected triol 3 is isolated with a yield of 60% after purification by chromatography on a silica gel column with elution by a hexane/ethyl acetate mixture 1:1.

Analyses:

MP 34-6° C.; $[\alpha]_D$ −14.6°; NMR $^1$H δ 0.70-1.10 (4H, m), 0.80 (3H, d, J=6.6 Hz), 0.91 (3H, d, J=6.6 Hz), 0.92 (3H, d, J=6.6 Hz), 1.2-1.9 (8H, m); 3.29 (1H, dd, J=6.6, 4.25 Hz), 3.71 (1H, dd, J.=12.0, 7.0 Hz), 3.88 (1H, m); NMR $^{13}$C δ 18.4, 21.9, 23.1, 23.9, 25.7, 30.5, 33.6, 38.3, 45.9, 61.0, 61.2, 65.7; mass spectrum: m/z 198, 183 (100%), 167, 155, 149, 139, 125, 119, 111, 105, 95, 81, 67, 55; IR spectrum (nujol): v (cm$^{-1}$) 896, 984, 1032, 1065, 3382.

The refreshing effect of this compound which can exist in the form of two isomers, 3a and 3b, is intense, and its bitterness remains practically imperceptible. The hydrophilic nature of this compound allows it to be used in the applications for which this property is sought.

The specific rotatory powers were measured at a concentration of 1% (weight/vol) in chloroform, and the NMR spectra were recorded with a spectrometer operating at 250 M Hz, with chloroform as solvent unless otherwise indicated.

COUNTER EXAMPLES

Compounds similar to those of the invention were also prepared.

When the synthesis methodology of Example 1 is applied to l-isomenthone, d-menthone or d-isomenthone, three pairs of diols are obtained with the configurations (1S,3R,4S) and (1S,3S,4S), (1S,3R,4R) and (1S,3S,4R), (1R,3R,4R) and (1R,3S,4R) respectively. All these diols have a refreshing effect, but none to a degree comparable to those prepared from l-menthone.

The diols 4, 5 and 6 hereafter have a reduced intensity of refreshing effect and a perceptible bitterness, which is even severe in the case of compound 4. The same drawbacks are observed in the case of 1,4-diol 7 and 1,5-diol 8 hereafter. The introduction of a methoxymethyl radical into the structure of the (1R,3R,4S)-3-hydroxy-p-menthane-3-ethanol, as in the case of the isomeric diols 9a and 9b hereafter, has the effect (especially for one of them), of increasing both the refreshing sensation and the bitterness.

Neither of the two isomers of the triol 10 produces a refreshing sensation to a degree of intensity comparable to that of diols 1, 2 or 3.

O-alkylated derivatives of (1R,3R,4S)-3-hydroxy-p-menthane-3-methanol and (1R,3R,4S)-3-hydroxy-p-menthane-3-ethanol are not endowed with a particularly intense refreshing effect and their bitterness is too significant, as in the case of diol 11.

The preparation of esters of the single primary alcohol function of (1R,3R,4S)-3-hydroxy-p-menthane-3-methanol or (1R,3R,4S)-3-hydroxy-p-menthane-3-ethanol, such as the acetate 12 and the mono-succinate 13, has led to compounds with disappointing qualities. The same is true for the mixed carbonates of (l)-menthol with (1R,3R,4S)-3-hydroxy-p-menthane-3-methanol 14, or with (1R,3R,4S)-3-hydroxy-p-menthane-3-ethanol 15.

COMPOSITION EXAMPLES

Example I

| 1 - Perfuming composition for after-shave lotion. | |
|---|---|
| Lavender essence | 250 |
| Dihydromyrcenol | 50 |
| Geranium essence | 20 |
| Pink brazilwood essence | 100 |
| Patchouli essence | 10 |
| Linalol | 100 |
| Linalyl acetate | 50 |
| Phenylethyl alcohol | 200 |
| Hexylcinnamic aldehyde | 50 |
| Ethylene brassylate | 100 |
| Coumarin | 50 |
| (−)-(1R,3R,4S)-3-hydroxy-p-menthane-3-ethanol | 20 |
| | 1000 g |

2—Use of this composition in the preparation of after-shave lotions, where between approximately 0.5 and 1% of this composition is used in the lotion of the formula below.

| | |
|---|---|
| Irgasan DP 300 | 0.15 |
| Allantoin | 0.2 |
| Propylene-glycol | 2 |
| 96° Alcohol | 45.3 |
| Perfuming composition | 0.5 |
| Cremophor RH 40 | 0.5-2 |
| Demineralized water | QS 100 g |

Example II

1—Perfuming Composition for Shaving Cream

| | |
|---|---|
| Redistilled *patchouli* essence | 220 |
| *Lavandin abrialis* essence | 90 |
| Celery seed essence | 70 |
| Phenylethyl alcohol | 70 |
| Frankincense resinoid | 100 |
| Galbanum resinoid | 60 |
| 10% methyl atrarate in ethyl citrate | 50 |
| Exaltolide | 10 |
| 50% hexahydro-hexamethylcyclopentabenzopyrane in ethyl citrate | 150 |
| Hexylcinnamic aldehyde | 120 |
| 3-hydroxy-p-menthane-3-(ethane-1,2-diol) | 60 |
| | 1000 g |

2—Use of this Perfuming Composition in the Preparation of Shaving Cream

Between approximately 0.5 and 1% of perfuming composition was used in the shaving cream of the following formula:

| | |
|---|---|
| Triple pressed stearin | 32.5 g |
| Fatty acids of coconut distilled from copra (UNIPROL) | 12.5 g |
| 70% sorbitol | 15 g |
| 100% soda = 1° i.e. 40% | 2.2 g |
| 100% potash | 8.2 g |
| Borax | 1 g |
| Neutral 40% sodium silicate | 1 g |
| Lanolin | 0.1 g |
| Perfuming composition | 1 g |
| Water | 26.5 g |

Example III

| | |
|---|---|
| Perfume for aerosol body deodorant | 100 |
| 4-t-butylmethylhydrocinnamic aldehyde | |
| Gamma methylionone | 10 |
| Eugenol | 5 |
| Linalol | 100 |
| Geraniol | 30 |
| Benzyl acetate | 50 |
| Vetiveryl acetate | 30 |
| Benzyl salicylate | 220 |
| 10% styrallyl acetate in ethyl citrate | 15 |
| Hexylcinnamic aldehyde | 120 |
| Cinnamic alcohol | 100 |
| Paraguay petitgrain essence | 100 |
| Ethylene brassylate | 100 |
| (−)-(1R,3R,4S)-3-hydroxy-p-menthane-3-methanol | 20 |
| | 1000 g |

This perfuming composition was used in an aerosol formulation such as:

| | |
|---|---|
| Irgasan DP300 | 0.5 |
| Isopropyl myristate | 11.5 |
| Perfume according to above formula | 0.2-1 |
| 96° alcohol | QS 100 |

The flask is filled 70% with the preceding mixture and 30% with aerosol propellant at 2.5 bars (propane/butane mixture).

Example IV

Flavouring Composition for Mouthwashes

Approximately 0.2 g of (−)-(1R,3R,4S)-3-hydroxy-p-menthane-3-methanol is used per litre of prepared mouthwash. A refreshing effect is obtained.

Example V

Flavouring Composition for Toothpastes

Approximately between 0.05 and 0.2% by weight of (−)-(1R,3R,4S)-3-hydroxy-p-menthane-3-methanol with respect to the finished product is used. A preferential embodiment envisages the addition of approximately 0.1 to 0.15% by weight of sodium saccharinate, used as sweetener in order to eliminate the slight bitterness which the composition may have.

Example VI

Flavouring Composition for Tobaccos

Approximately 0.05 g of (−)-(1R,3R,4S)-3-hydroxy-p-menthane-3-ethanol is used per kilogram of tobacco. A refreshing effect is obtained.

Example VII

Flavouring Composition for Boiled Sweets

A solution of saccharose (350 g) in water (110 g) is prepared which is boiled at 107° C. 150 g of glucose syrup is added and boiled at 148° C. The flavouring, citric acid and colouring agent are added at a temperature of approximately 120°, and 0.2 g of (−)-(1R,3R,4S)-3-hydroxy-p-menthane-3-methanol is added per kilogramme of final product. A very distinct refreshing effect is obtained.

Example VIII

Flavouring Composition of Chewing-Gums 0.2 to 0.8 g of (−)-(1R,3R,4S)-3-hydroxy-p-menthane-3-methanol per kilogram of finished product is added to a chewing-gum paste prepared according to the usual procedure.

Formulas of the compounds identified according to the present invention appear below:

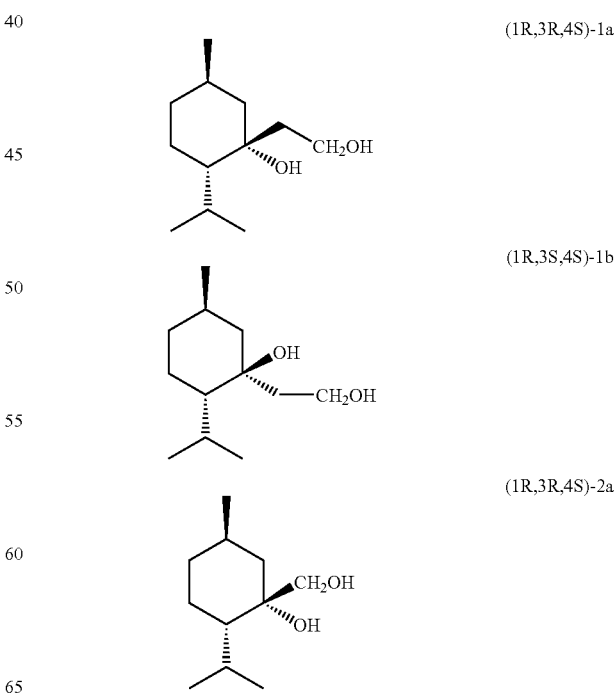

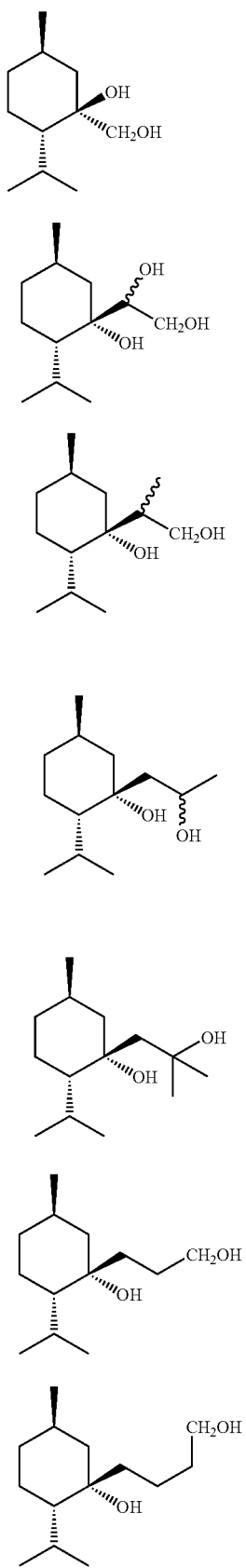
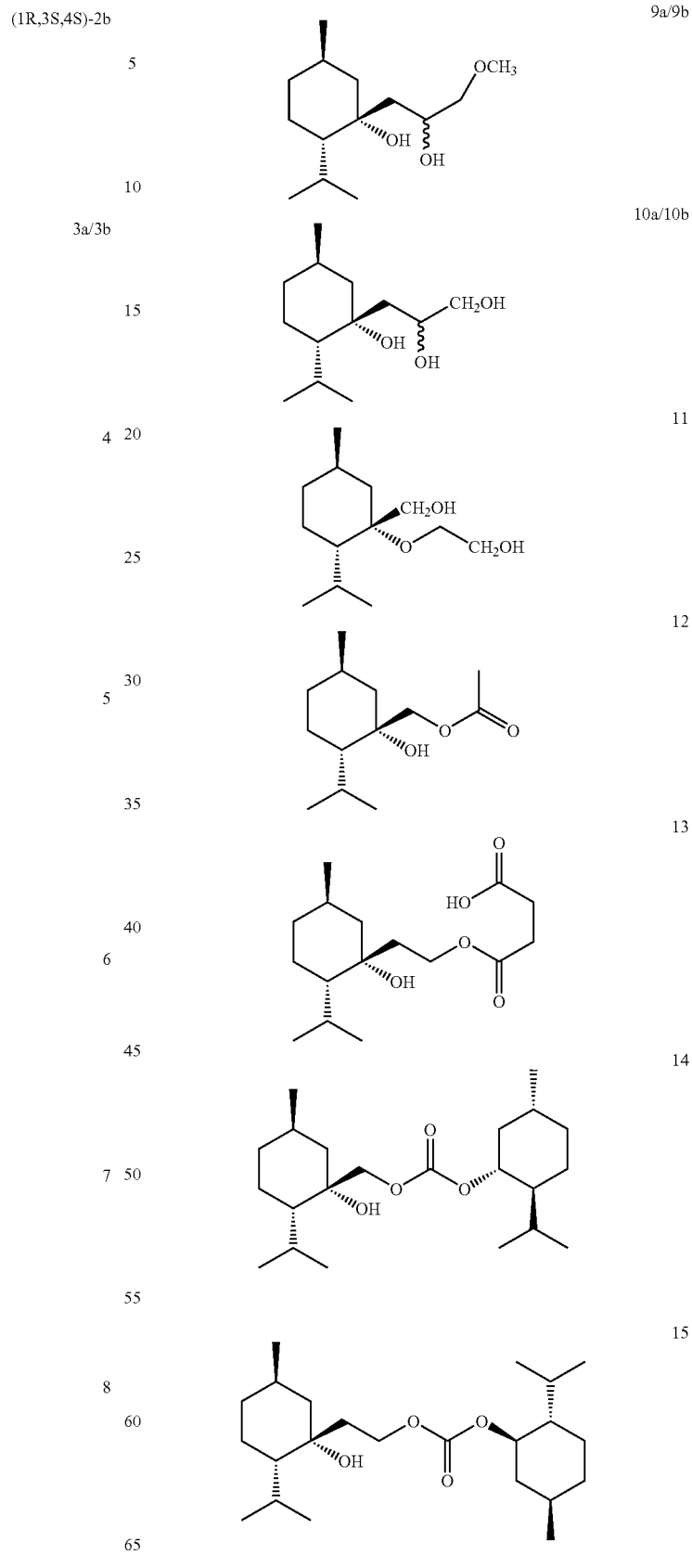

The invention claimed is:

1. A 3-alkylated (1R,4S)-p-menthan-3-ol derivative, of formula A or B,

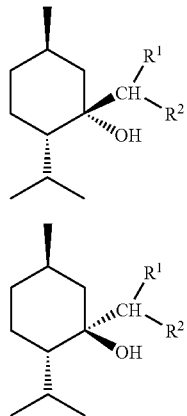

in which,
when $R^2$ represents hydrogen or a methyl radical, $R^1$ represents a —$(CH_2)$n-OH group where n can take the values 0, 1, 2, and 3, or
when $R^2$ represents a hydroxy radical, $R^1$ represents a methyl radical or a —$(CH_2)$n-OH group where n can take the values 1, 2, and 3, and
wherein said 3-alkylated (1R,4S)-p-menthan-3-ol derivative is crystallized.

2. A derivative according to claim 1, characterized in that $R^2$ represents hydrogen or a methyl radical.

3. A derivative according to claim 1, characterized in that $R^2$ represents a hydroxy radical.

4. A derivative according to claim 1, characterized in that n has the value 0 or 1.

5. A derivative according to claim 1 selected from the group consisting of:
(−)-(1R,3R,4S)-3-hydroxy-p-menthane-3-ethanol,
(−)-(1R,3S,4S)-3-hydroxy-p-menthane-3-ethanol,
(−)-(1R,3R,4S)-3-hydroxy-p-menthane-3-methanol, and
(−)-(1R,3S,4S)-3-hydroxy-p-menthane-3-methanol.

6. A process for the preparation of a 3-alkylated crystallized (1R,4S)-p-menthan-3-ol derivative of formula A or B according to claim 1 in which $R^2$ represents H and $R^1$ represents a —$(CH_2)$n-OH group where n is equal to 1, characterized in that a Reformatzky reaction is carried out between an alkyl α-halogenoacetate and more than 95% pure (−)-menthone, followed by the reduction of the β-hydroxyester thus obtained to 1,3-diol using a hydride in order to obtain the expected 3-hydroxy-p-menthan-3-ethanol isomers which are isolated if desired.

7. A process for the preparation of a 3-alkylated crystallized (1R,4S)-p-menthan-3-ol derivative of formula A according to claim 1 in which $R^2$ represents hydrogen and $R^1$ represents a —$(CH_2)$n-OH group where n=0, characterized in that a vinylmagnesium halide is condensed with (−)-menthone, followed by acetylation of the tertiary vinylcarbinol obtained, then by an ozonolysis process in order to obtain an ozonide which is reduced, then hydrolysis of the acetate thus formed, in order to obtain the expected 1,2-diol, which is isolated and if desired purified.

8. A process for the preparation of a 3-alkylated crystallized (1R,4S)-p-menthan-3-ol derivative of formula B according to claim 1 in which $R^2$ represents hydrogen and $R^1$ represents a —$(CH_2)$n-OH group where n=0 characterized in that a (−)-menthone cyanhydrin is selectively prepared, which is then reduced with a hydride in order to obtain the expected derivative, which is isolated and if desired purified.

9. A process for the preparation of a 3-alkylated crystallized (1R,4S)-p-menthan-3-ol derivative of formula A according to claim 1 in which $R^2$ represents a hydroxy radical and $R^1$ represents a —$(CH_2)$n-OH group where n=0 characterized in that a vinylmagnesium halide, is condensed with (−)-menthone, followed by epoxidation of the tertiary vinylcarbinol obtained, then alkaline hydrolysis is carried out, in order to obtain the expected derivative, which is isolated and if desired purified.

10. A perfume or cosmetic composition, characterized in that it contains a p-menthane-3-ol derivative as defined in claim 1.

11. A food composition characterized in that it contains a p-menthane-3-ol derivative as defined in claim 1.

12. A perfume or cosmetic composition, further comprising a p-menthane-3-ol derivative as defined in claim 2.

13. A perfume or cosmetic composition, further comprising a p-menthane-3-ol derivative as defined in claim 3.

14. A perfume or cosmetic composition, further comprising a p-menthane-3-ol derivative as defined in claim 4.

15. A perfume or cosmetic composition, further comprising a p-menthane-3-ol derivative as defined in claim 5.

16. A food composition, further comprising a p-menthane-3-ol derivative as defined in claim 2.

17. A food composition, further comprising a p-menthane-3-ol derivative as defined in claim 3.

18. A food composition, further comprising a p-menthane-3-ol derivative as defined in claim 4.

19. A food composition, further comprising a p-menthane-3-ol derivative as defined in claim 5.

* * * * *